(12) United States Patent
Yang et al.

(10) Patent No.: US 8,840,993 B2
(45) Date of Patent: Sep. 23, 2014

(54) CURABLE POLYSILOXANE COATING COMPOSITION

(75) Inventors: Yu Yang, Eden Prairie, MN (US); Michael A. Semonick, White Bear Lake, MN (US); George G. I. Moore, Afton, MN (US); Larry D. Boardman, Woodbury, MN (US); Michele A. Craton, Cottage Grove, MN (US); Kanta Kumar, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 13/807,326

(22) PCT Filed: Jun. 21, 2011

(86) PCT No.: PCT/US2011/041181
§ 371 (c)(1),
(2), (4) Date: Dec. 28, 2012

(87) PCT Pub. No.: WO2012/003108
PCT Pub. Date: Jan. 5, 2012

(65) Prior Publication Data
US 2013/0101840 A1    Apr. 25, 2013

Related U.S. Application Data

(60) Provisional application No. 61/359,985, filed on Jun. 30, 2010, provisional application No. 61/360,019, filed on Jun. 30, 2010, provisional application No. 61/480,598, filed on Apr. 29, 2011.

(51) Int. Cl.
| | |
|---|---|
| C09D 183/06 | (2006.01) |
| C08G 77/12 | (2006.01) |
| C07F 9/6584 | (2006.01) |
| C08L 83/04 | (2006.01) |
| C07C 279/04 | (2006.01) |
| C07C 267/00 | (2006.01) |
| C07F 9/06 | (2006.01) |
| C09D 183/04 | (2006.01) |
| C07F 9/572 | (2006.01) |
| C08G 77/24 | (2006.01) |
| C08K 5/5399 | (2006.01) |

(52) U.S. Cl.
CPC .............. *C09D 183/06* (2013.01); *C08G 77/24* (2013.01); *C07F 9/65846* (2013.01); *C08L 83/04* (2013.01); *C07F 9/6584* (2013.01); *C07C 279/04* (2013.01); *C07C 267/00* (2013.01); *C08K 5/5399* (2013.01); *C07F 9/065* (2013.01); *C09D 183/04* (2013.01); *C07F 9/5721* (2013.01)
USPC ............ 428/345; 524/588; 524/503; 427/387

(58) Field of Classification Search
None
See application file for complete search history.

(56) References Cited

U.S. PATENT DOCUMENTS

| | | |
|---|---|---|
| 2,708,289 A | 5/1955 | Collings |
| 3,328,482 A | 6/1967 | Northrup et al. |
| 3,445,417 A | 5/1969 | Layne et al. |
| 3,628,996 A | 12/1971 | Weber |
| 3,969,543 A | 7/1976 | Roberts et al. |
| 4,181,752 A | 1/1980 | Martens et al. |
| 4,269,963 A | 5/1981 | Homan et al. |
| 4,489,199 A | 12/1984 | Wengrovius |
| 4,761,443 A | 8/1988 | Lopes |
| 5,219,958 A | 6/1993 | Noomen et al. |
| 5,286,815 A | 2/1994 | Leir et al. |
| 5,371,162 A | 12/1994 | Konings et al. |
| 5,403,909 A | 4/1995 | Rubinsztajn |
| 5,688,888 A | 11/1997 | Burkus, II et al. |
| 5,789,460 A | 8/1998 | Harkness et al. |
| 5,820,944 A | 10/1998 | Harkness et al. |
| 5,866,222 A | 2/1999 | Seth et al. |
| 5,891,529 A | 4/1999 | Harkness et al. |
| 6,096,483 A | 8/2000 | Harkness et al. |
| 6,124,371 A | 9/2000 | Stanssens et al. |
| 6,136,996 A | 10/2000 | Rubinsztajn et al. |
| 6,166,207 A | 12/2000 | Friedrich et al. |
| 6,204,350 B1 | 3/2001 | Liu et al. |
| 6,235,832 B1 | 5/2001 | Deng et al. |
| 6,277,986 B1 | 8/2001 | Hall-Goulle et al. |
| 6,551,761 B1 | 4/2003 | Hall-Goulle et al. |
| 6,777,512 B1 | 8/2004 | Sonnenschein et al. |
| 6,780,484 B2 | 8/2004 | Kobe et al. |
| 6,805,933 B2 | 10/2004 | Patel et al. |
| 6,835,422 B2 | 12/2004 | Kobe et al. |

(Continued)

FOREIGN PATENT DOCUMENTS

| | | |
|---|---|---|
| EP | 0 444 633 A2 | 9/1991 |
| JP | 61022094 A | 1/1986 |

(Continued)

OTHER PUBLICATIONS

Org. Lett. 9, No. 1, pp. 1-169 (2007).

(Continued)

*Primary Examiner* — Robert S Loewe
(74) *Attorney, Agent, or Firm* — Lucy C. Weiss

(57) ABSTRACT

A curable composition comprises (a) at least one polydiorganosiloxane, fluorinated polydiorganosiloxane, or combination thereof comprising reactive silane functionality comprising at least two hydroxysilyl moieties; (b) at least one polydiorganosiloxane, fluorinated polydiorganosiloxane, or combination thereof comprising reactive silane functionality comprising at least two hydrosilyl moieties; and (c) at least one base selected from amidines, guanidines, phosphazenes, proazaphosphatranes, and combinations thereof; wherein at least one of the components (a) and (b) has an average reactive silane functionality of at least three.

20 Claims, No Drawings

(56) References Cited

U.S. PATENT DOCUMENTS

| | | |
|---|---|---|
| 7,064,173 B2 | 6/2006 | Rubinsztajn et al. |
| 7,148,370 B1 | 12/2006 | Rubinsztajn et al. |
| 7,300,747 B2 | 11/2007 | Okazaki et al. |
| 7,332,541 B2 | 2/2008 | Schindler et al. |
| 7,482,391 B1 | 1/2009 | Cross et al. |
| 7,538,104 B2 | 5/2009 | Baudin et al. |
| 2001/0037008 A1 | 11/2001 | Sherman et al. |
| 2004/0242867 A1 | 12/2004 | Baudin et al. |
| 2006/0014844 A1 | 1/2006 | Lim et al. |
| 2006/0111505 A1 | 5/2006 | Schindler et al. |
| 2009/0171025 A1 | 7/2009 | Matsushita et al. |
| 2010/0036049 A1 | 2/2010 | Matsushita et al. |
| 2010/0041810 A1 | 2/2010 | Wakabayashi et al. |
| 2011/0028585 A1 | 2/2011 | Shiraishi et al. |
| 2011/0098392 A1 | 4/2011 | Barrandon et al. |
| 2013/0101840 A1 | 4/2013 | Yang et al. |
| 2013/0101841 A1 | 4/2013 | Yang et al. |
| 2013/0102728 A1 | 4/2013 | Yang et al. |

FOREIGN PATENT DOCUMENTS

| | | |
|---|---|---|
| WO | WO 2004/022618 A1 | 3/2004 |
| WO | WO 2007/149422 A2 | 12/2007 |
| WO | WO 2009/122664 A1 | 10/2009 |
| WO | WO 2010/146254 A1 | 12/2010 |
| WO | WO 2010/149869 A1 | 12/2010 |
| WO | WO 2012/003152 A1 | 1/2012 |

OTHER PUBLICATIONS

E. Lukevics and M. Dzintara, "Silylation of Hydroxyl-Containing Compounds with Aryl and Heteroaryl-Hydrosilanes in the Presence of Amines," Journal of Organometallic Chemistry 271, pp. 307-317 (1984).

Kanji et al., "Quaternary Ammonium Salt as DBU-Generating Photobase Generator", Journal of Photopolymer Science and Technology, 19(1), 81-84 (Jan. 1, 2006).

International Search Report for PCT Application No. PCT/US2011/041181, filed Jun. 21, 2011, 4 pp.

Chemtob et al., "UV-Activated Silicone Oligomer Cross-Linking Through Photoacid and Photobase Organocatalysts," *J. Appl. Polym. Sci.* 2013, 6 pages.

Suyama et al., "Photobase Generators: Recent Progress and Application Trend in Polymer Systems," *Progress in Polymer Science* 34 (2009) 194-209.

CURABLE POLYSILOXANE COATING COMPOSITION

STATEMENT OF PRIORITY

This application is a 371 of PCT/US2011/041180, filed on Jun. 21, 2011. This application claims the priorities of U.S. Provisional Applications Nos. 61/360,019, filed Jun. 30, 2010; 61/359,985, filed Jun. 30, 2010; and 61/480,598, filed Apr. 29, 2011; the contents of which are hereby incorporated by reference.

FIELD

This invention relates to curable coating compositions comprising reactive silane functionality and, in other aspects, to processes for coating the compositions and articles prepared thereby.

BACKGROUND

Moisture-curable polysiloxane compositions cure in the presence of moisture to form crosslinked materials such as release coatings and surface treatments that are useful in many industries. For example, a polysiloxane or fluorinated polysiloxane is often selected to provide moisture-curable release coatings suitable for use with pressure-sensitive adhesives. The moisture for curing is typically obtained from the atmosphere or from a substrate to which the composition has been applied, although it can also be added to the composition (for example, to enable curing in depth or in confinement).

Moisture-curable polysiloxane compositions usually comprise siloxane polymers having groups (for example, alkoxysilyl or acyloxysilyl moieties) that can react in the presence of moisture to form cured (that is, crosslinked) materials. Moisture-curable compositions comprising alkoxysilyl or acyloxysilyl functionality typically cure in two reactions. In the first reaction, the alkoxysilyl or acyloxysilyl groups hydrolyze in the presence of moisture and a catalyst to form silanol compounds having hydroxysilyl groups. In the second reaction, the hydroxysilyl groups condense with other hydroxysilyl, alkoxysilyl, or acyloxysilyl groups in the presence of a catalyst to form —Si—O—Si— linkages. The two reactions occur essentially simultaneously upon generation of the silanol compound. Commonly used catalysts for the two reactions include Bronsted and Lewis acids. A single material can catalyze both reactions.

Preferably, the hydrolysis and condensation reactions proceed quickly after the moisture-curable composition has been applied, for example, to a substrate. At the same time, however, the reactions must not occur prematurely, for example, during processing or storage.

A good balance between these properties is often difficult to obtain, as rapid reactivity and storage stability are opposite properties to each other. For example, highly active catalysts such as tetraalkyl titanate esters rapidly accelerate the moisture-curing reaction but, at the same time, can make it difficult to process the materials without risking premature gelation in feed tanks, coating equipment, and other manufacturing and handling apparatus. Control of the amount of moisture can be critical, with too little moisture potentially resulting in slow or incomplete cure and too much moisture resulting in premature cure.

A variety of approaches have been used for providing moisture-curable compositions that have acceptable cure rates without processing and storage difficulties. For example, two-part systems have been developed (one part comprising a functional siloxane polymer and the other part comprising a catalyst), with the two parts being mixed immediately prior to use. While this approach has been useful in small-scale applications, it has been less efficient for large-scale manufacturing, where delays caused by having to mix the two parts have been undesirable. Furthermore, coating operations must be completed expeditiously before the composition cures in the pot, and this has been difficult when working with large surface area substrates or a large volume of composition.

Ammonium salt catalysts have been developed that are inactive until heated sufficiently to liberate an acid compound that initiates the moisture curing reaction. Liberation of the acid also generates an amine, however, that must be removed by evaporation. In addition, the heat used to activate the catalyst can damage heat-sensitive substrates onto which the composition has been applied.

Other materials (for example, onium salts such as sulfonium and iodonium salts) have been used to generate acid species in situ upon irradiation (for example, irradiation with ultraviolet light). Such materials have not required heat activation and therefore have enabled the use of heat-sensitive substrates without damage (and without the production of undesirable species requiring removal), but the materials have been relatively expensive, have exhibited cure inhibition on some substrates, and have required moisture control and the use of coating equipment with irradiation capability.

Conventional tin catalysts such as dibutyl tin dilaurate can provide stable curable polysiloxane compositions that can be processed and coated without premature gelation. In addition to typical moisture-curable systems, it has been found that curable compositions comprising dual reactive silane functionality in the form of hydrosilyl and hydroxysilyl groups (dehydrogenatively-curable systems) can be cured by using tin catalysts. The compositions have been widely used for pressure-sensitive adhesive and mold release applications but have sometimes suffered from relatively short pot lives. In addition, the use of tin catalysts is becoming particularly problematic because the organotin compounds generally employed as catalysts are now considered to be toxicologically objectionable.

Acceleration of cure has been achieved by the use of compounds such as substituted guanidines, diorganosulfoxides, imidazoles, amidines, and amines in combination with tin catalysts in room temperature vulcanizing silicone compositions. Amine compounds including amidines have also been proposed for use in the absence of tin catalysts for curing moisture-curable, silyl-functional organic polymers, but practical curability of alkoxysilyl-functional organic polymers and acceptable adhesion to substrates were achieved only with strongly basic amines (those exhibiting a pH of at least 13.4 in aqueous solution).

SUMMARY

Thus, we recognize that there exists an ongoing need for curable polysiloxane compositions that can provide acceptable cure rates without significant processing and storage difficulties (for example, due to premature gelation). Preferably, these compositions will be efficiently processable (for example, without the need for mixing of a two-part system prior to cure), will employ catalysts that do not generate species requiring removal, and/or will not require heat activation (so as to enable curing at relatively low temperatures and/or the use of heat-sensitive substrates). Ideally, the compositions will employ catalysts that are relatively non-toxic, provide compositions that are relatively stable in solution but relatively fast-curing upon drying, effective in relatively low concentrations, and/or effective under relatively low (or no) moisture conditions.

Briefly, in one aspect, this invention provides a curable polysiloxane composition comprising dual reactive silane functionality. The composition comprises (a) at least one polydiorganosiloxane, fluorinated polydiorganosiloxane, or combination thereof comprising reactive silane functionality comprising at least two hydroxysilyl moieties (that is, monovalent moieties comprising a hydroxyl group bonded directly to a silicon atom);

(b) at least one polydiorganosiloxane, fluorinated polydiorganosiloxane, or combination thereof comprising reactive silane functionality comprising at least two hydrosilyl moieties (that is, monovalent moieties comprising a hydrogen atom bonded directly to a silicon atom); and (c) at least one base selected from amidines, guanidines, phosphazenes, proazaphosphatranes, and combinations thereof;

wherein at least one of components (a) and (b) has an average reactive silane functionality of at least three (that is, component (a) has at least three hydroxysilyl moieties (on average), component (b) has at least three hydrosilyl moieties (on average), or both). Components (a) and (b) preferably comprise at least one polydiorganosiloxane (more preferably, at least one polydialkylsiloxane; most preferably, at least one polydimethylsiloxane).

Preferably, component (a) is hydroxyl-endblocked, so as to comprise two terminal hydroxysilyl moieties (on average). The base preferably comprises at least one amidine (most preferably, 1,8-diazabicyclo[5.4.0]-7-undecene (DBU)). The composition preferably further comprises at least one solvent (for example, an aprotic organic solvent such as heptane).

It has been discovered that, unlike standard amine bases such as 4,4'-trimethylenebis(1-methylpiperidine) (which are ineffective), the above-described bases can effectively catalyze the curing (apparently, by condensation) of polysiloxane compositions comprising reactive silane functionality in the form of hydrosilyl and hydroxysilyl moieties. The bases can provide relatively rapid cure (for example, upon removal of solvent curing can occur within periods of time as short as about 1 minute) even at temperatures as low as ambient (for example, about 23° C.), without the need for heat activation, and can be effective in relatively small amounts (for example, at concentrations as low as about 0.5 weight percent or less, based upon the total weight of components (a), (b), and (c)). Thus, polysiloxane compositions comprising the bases can be suitable for use in high speed coating and curing operations in an industrial setting, without the need for addition of heat. In spite of such effective curability, the compositions can exhibit relatively good storage stability (for example, for a period of weeks in a closed container) and/or relatively long pot life (for example, on the order of 8 hours or more) in a variety of solvents (for example, heptane, methyl ethyl ketone, or a combination thereof), without the need for mixing of a two-part system immediately prior to use.

In surprising contrast with prior art compositions, the bases can be effective in the curable polysiloxane composition of the invention in the substantial absence of other condensation catalysts and/or in the substantial absence of moisture. The bases can be used as substitutes for conventional tin catalysts to provide organometallic catalyst-free, curable polysiloxane compositions, without the need for changes in the nature of the polysiloxane components of conventional tin-cured polysiloxane compositions (for example, release coating compositions such as Syl-Off™ 292 coating composition, available from Dow Corning Corporation, Midland, Mich.). Unlike the conventional tin catalysts, at least some of the bases (for example, DBU) are relatively non-toxic and therefore suitable for use in preparing relatively environmentally friendly or "green" polysiloxane compositions.

The curable polysiloxane composition of the invention can be cured to provide crosslinked networks having properties that can be tailored to the requirements of various different applications (for example, by varying the natures, relative amounts, and/or degrees of reactive silane functionality of starting components (a) and/or (b)). Thus, the curable polysiloxane composition can be used to provide coatings having a variety of surface properties for use in numerous coating applications (for example, use as release coatings for pressure-sensitive adhesives, protective coatings, water- and/or oil-repellent coatings or surface treatments, and the like). The curable polysiloxane composition of the invention can be particularly useful in relatively sensitive applications requiring careful and/or tailored control of surface properties (for example, release coating applications), as the base catalysts do not appear to produce species requiring removal and, in some embodiments, the base catalysts are sufficiently volatile to be evaporated from the composition during processing, thereby leaving essentially no catalyst contamination in the cured material (in contrast with the metal contamination of conventional tin catalysts, which can be particularly problematic in the area of electronics).

In view of the foregoing, at least some embodiments of the curable polysiloxane composition of the invention meet the above-described, ongoing need for curable compositions that can provide acceptable cure rates without significant processing and storage difficulties (for example, being relatively stable in solution but relatively fast-curing upon drying), while also being efficiently processable (for example, without the need for mixing of a two-part system prior to cure, for contaminant removal, and/or for heat activation). At least some embodiments of the curable polysiloxane composition also employ catalysts that are relatively non-toxic, while being effective in relatively low concentrations and/or under relatively low (or no) moisture conditions.

In another aspect, this invention also provides a coating process comprising (a) providing the above-described curable polysiloxane composition of the invention;

(b) providing at least one substrate having at least one major surface;

(c) applying the curable polysiloxane composition to at least a portion of at least one major surface of the substrate; and (d) allowing or inducing the curable polysiloxane composition to cure to form a coating.

In yet another aspect, this invention provides an article comprising at least one substrate having at least one major surface, the substrate bearing, on at least a portion of at least one major surface, a coating prepared by the above-described coating process.

DETAILED DESCRIPTION

In the following detailed description, various sets of numerical ranges (for example, of the number of carbon atoms in a particular moiety, of the amount of a particular component, or the like) are described, and, within each set, any lower limit of a range can be paired with any upper limit of a range. Such numerical ranges also are meant to include all numbers subsumed within the range (for example, 1 to 5 includes 1, 1.5, 2, 2.75, 3, 3.80, 4, 5, and so forth).

As used herein, the term "and/or" means one or all of the listed elements or a combination of any two or more of the listed elements.

The words "preferred" and "preferably" refer to embodiments of the invention that may afford certain benefits under certain circumstances. Other embodiments may also be preferred, however, under the same or other circumstances. Furthermore, the recitation of one or more preferred embodiments does not imply that other embodiments are not useful, and is not intended to exclude other embodiments from the scope of the invention.

The term "comprises" and variations thereof do not have a limiting meaning where these terms appear in the description and claims.

As used herein, "a," "an," "the," "at least one," and "one or more" are used interchangeably.

The above "Summary of the Invention" section is not intended to describe every embodiment or every implementation of the invention. The detailed description that follows more particularly describes illustrative embodiments. Throughout the detailed description, guidance is provided through lists of examples, which examples can be used in various combinations. In each instance, a recited list serves only as a representative group and should not be interpreted as being an exclusive list.

DEFINITIONS

As used in this patent application:

"catenated heteroatom" means an atom other than carbon (for example, oxygen, nitrogen, or sulfur) that replaces one or more carbon atoms in a carbon chain (for example, so as to form a carbon-heteroatom-carbon chain or a carbon-heteroatom-heteroatom-carbon chain);

"cure" means conversion to a crosslinked polymer network (for example, through catalysis);

"fluoro-" (for example, in reference to a group or moiety, such as in the case of "fluoroalkylene" or "fluoroalkyl" or "fluorocarbon") or "fluorinated" means only partially fluorinated such that there is at least one carbon-bonded hydrogen atom;

"fluorochemical" means fluorinated or perfluorinated;

"heteroorganic" means an organic group or moiety (for example, an alkyl or alkylene group) containing at least one heteroatom (preferably, at least one catenated heteroatom);

"hydrosilyl" refers to a monovalent moiety or group comprising a silicon atom directly bonded to a hydrogen atom (for example, the hydrosilyl moiety can be of formula —Si(R)$_{3-p}$(H)$_p$, where p is an integer of 1, 2, or 3 and R is a hydrolyzable or non-hydrolyzable group (preferably, non-hydrolyzable) such as alkyl or aryl);

"hydroxysilyl" refers to a monovalent moiety or group comprising a silicon atom directly bonded to a hydroxyl group (for example, the hydroxysilyl moiety can be of formula —Si(R)$_{3-p}$(OH)$_p$ where p is an integer of 1, 2, or 3 and R is a hydrolyzable or non-hydrolyzable group (preferably, non-hydrolyzable) such as alkyl or aryl);

"isocyanato" means a monovalent group or moiety of formula —NCO;

"mercapto" means a monovalent group or moiety of formula —SH;

"oligomer" means a molecule that comprises at least two repeat units and that has a molecular weight less than its entanglement molecular weight; such a molecule, unlike a polymer, exhibits a significant change in properties upon the removal or addition of a single repeat unit;

"oxy" means a divalent group or moiety of formula —O—; and

"perfluoro-" (for example, in reference to a group or moiety, such as in the case of "perfluoroalkylene" or "perfluoroalkyl" or "perfluorocarbon") or "perfluorinated" means completely fluorinated such that, except as may be otherwise indicated, there are no carbon-bonded hydrogen atoms replaceable with fluorine.

Component (a)

Polysiloxanes suitable for use as component (a) of the curable polysiloxane composition of the invention include polydiorganosiloxanes, fluorinated polydiorganosiloxanes, and combinations thereof (preferably, polydiorganosiloxanes) comprising reactive silane functionality comprising at least two hydroxysilyl moieties (that is, monovalent moieties comprising a hydroxyl group bonded directly to a silicon atom). The polysiloxanes can be oligomers, polymers, or a combination thereof. Preferably, the polysiloxanes are polymers, which can be linear, branched, or cyclic. Useful polymers include those that have random, alternating, block, or graft structures, or a combination thereof.

The molecular weight and the reactive silane functionality of component (a) (including the number and nature of the hydroxysilyl moieties) of the polysiloxanes can vary widely, depending upon, for example, the molecular weight and the reactive silane functionality of component (b) and the properties desired for the curable and/or cured composition. At least one of components (a) and (b) has an average reactive silane functionality of at least three, however (that is, component (a) has at least three hydroxysilyl moieties (on average), component (b) has at least three hydrosilyl moieties (on average), or both), so as to enable the formation of a crosslinked network.

Preferably, the polydiorganosiloxanes, fluorinated polydiorganosiloxanes, and combinations thereof used for component (a) are hydroxyl-endblocked, so as to comprise two terminal hydroxysilyl moieties (on average). The polysiloxanes preferably have a weight average molecular weight of about 150 to about 1,000,000 (more preferably, about 1,000 to about 1,000,000).

A preferred class of useful polysiloxanes includes those that can be represented by the following general formula:

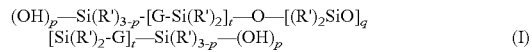
[Si(R')$_2$-G]$_t$—Si(R')$_{3-p}$—(OH)$_p$   (I)

wherein each p is independently an integer of 1, 2, or 3 (preferably, 1); each G is independently a divalent linking group; each R' is independently selected from alkyl, alkenyl, fluoroalkyl, aryl, fluoroaryl, cycloalkyl, fluorocycloalkyl, heteroalkyl, heterofluoroalkyl, heteroaryl, heterofluoroaryl, heterocycloalkyl, heterofluorocycloalkyl, and combinations thereof; q is an integer of 0 to about 15,000 (preferably, about 20 to about 15,000); and each t is independently an integer of 0 or 1 (preferably, 0). Preferably, each R' is independently selected from alkyl (preferably, having 1 to about 8 carbon atoms), fluoroalkyl (preferably, having 3 to about 8 carbon atoms; more preferably, R$_f$C$_2$H$_4$—, wherein R$_f$ is a fluorinated or perfluorinated alkyl group having 1 to about 6 carbon atoms (preferably, 1 to about 6 carbon atoms)), aryl, and combinations thereof. More preferably, each R' is independently selected from methyl, C$_4$F$_9$C$_2$H$_4$—, C$_6$F$_{13}$C$_2$H$_4$—, CF$_3$C$_2$H$_4$—, phenyl, C$_6$H$_5$C$_2$H$_4$—, and combinations thereof (even more preferably, methyl, CF$_3$C$_2$H$_4$—, phenyl, C$_4$F$_9$C$_2$H$_4$—, and combinations thereof; most preferably, methyl). Each divalent linking group, G, is preferably independently selected from oxy, alkylene, arylene, heteroalkylene, heteroarylene, cycloalkylene, heterocycloalkylene, and combinations thereof (more preferably, selected from oxy, alkylene, arylene, and combinations thereof). Heteroatoms (in G and/or R') can include oxygen, sulfur, nitrogen, phosphorus, and combinations thereof (preferably, oxygen, sulfur, and combinations thereof; more preferably, oxygen). G can contain fluorine, provided that it is separated from silicon by at least two carbon atoms.

Preferred polysiloxanes include hydroxyl-endblocked polydimethylsiloxane homopolymer, as well as hydroxyl-endblocked copolymers comprising dimethylsiloxane units and up to about 40 or 50 mole percent of other units selected from dialkylsiloxane units, (alkyl)(methyl)siloxane units, and (alkyl)(phenyl)siloxane units wherein each alkyl group is independently selected from alkyl groups having two to about 8 carbon atoms (for example, hexyl), di(fluoroalkyl)siloxane units, (fluoroalkyl)(methyl)siloxane units, and (fluoroalkyl)(phenyl)siloxane units wherein each fluoroalkyl group is independently selected from fluoroalkyl groups having 3 to about 8 carbon atoms (for example, trifluoropropyl or nonafluorohexyl), diphenylsiloxane units, and combinations thereof.

The polysiloxanes useful as component (a) can be used in the curable composition of the invention singly or in the form of mixtures of different polysiloxanes. Sometimes mixtures can be preferred. A preferred composition for use as component (a) comprises a mixture of (1) at least one polydiorganosiloxane, fluorinated polydiorganosiloxane, or combination thereof (preferably, at least one polydiorganosiloxane) having a weight average molecular weight in the range of about 300,000 to about 1,000,000 (more preferably, about 400,000 to about 900,000; most preferably, about 500,000 to about 700,000) and (2) at least one polydiorganosiloxane, fluorinated polydiorganosiloxane, or combination thereof (preferably, at least one polydiorganosiloxane) having a weight average molecular weight in the range of about 150 to about 150,000 (more preferably, about 10,000 to about 120,000; most preferably, about 10,000 to about 15,000). The relative amounts of component (1) and component (2) and their molecular weights can be selected for release applications according to the nature of the adhesive (or other material) to be utilized and the level of release desired.

For example, for mold release applications, the weight ratio of the former polysiloxane to the latter polysiloxane can range from about 3:1 to about 19:1 (preferably, about 4:1 to about 9:1; more preferably, about 6:1). For pressure sensitive adhesive (PSA) release applications, the weight ratio of the former polysiloxane to the latter polysiloxane can range, for example, from about 2:1 to about 1:10 (preferably, about 1:1 to about 1:6; more preferably, about 1:2 to about 1:4).

The polysiloxanes suitable for use as component (a) can be prepared by known synthetic methods and many are commercially available. For example, the hydroxysilyl-functional components of Syl-Off™ 292 coating composition (available from Dow Corning Corporation, Midland, Mich.) are preferred polysiloxanes, and other useful polysiloxanes of varying molecular weight can be obtained from Gelest, Inc., Morrisville, Pa. (see, for example, the polysiloxanes described in Silicon Compounds: Silanes and Silicones, Second Edition, edited by B. Arkles and G. Larson, Gelest, Inc. (2008)).

Component (b)

Polysiloxanes suitable for use as crosslinker component (b) of the curable composition of the invention include polydiorganosiloxanes, fluorinated polydiorganosiloxanes, and combinations thereof comprising reactive silane functionality comprising at least two hydrosilyl moieties (that is, monovalent moieties comprising a hydrogen atom bonded directly to a silicon atom). The polysiloxanes can be small molecules, oligomers, polymers, or a combination thereof. Preferably, the polysiloxanes are polymers. The polysiloxanes can be linear, branched, or cyclic. Useful polymers include those that have random, alternating, block, or graft structures, or a combination thereof.

The molecular weight and the reactive silane functionality of component (b) (including the number and nature of the hydrosilyl moieties) can vary widely, depending upon, for example, the molecular weight and the reactive silane functionality of component (a) and the properties desired for the curable and/or cured composition. Preferably, component (b) has an average reactive silane functionality of at least three (so as to enable the formation of a crosslinked network when component (a) is hydroxyl-endblocked). The polysiloxanes preferably have a weight average molecular weight of about 100 to about 100,000.

A preferred class of polysiloxanes includes those that can be represented by the following general formula:

$$R'_2R''SiO(R'_2SiO)_r(HR'SiO)_sSiR''R'_2 \quad (II)$$

wherein R' is as defined above for Formula (I); each R" is independently hydrogen or R'; r is an integer of 0 to about 150 (preferably, 0 to about 100; more preferably, 0 to about 20); and s is an integer of 2 to about 150 (preferably, about 5 to about 100; more preferably, about 20 to about 80). Most preferably, both R" and R' are methyl, r is 0, and/or s is about 40.

Preferred hydride-functional polysiloxanes include those comprising polydimethylsiloxane homopolymer, as well as those comprising copolymer(s) comprising dimethylsiloxane units and up to about 40 or 50 mole percent of other units selected from dialkylsiloxane units, (alkyl)(methyl)siloxane units, and (alkyl)(phenyl)siloxane units wherein each alkyl group is independently selected from alkyl groups having two to about 8 carbon atoms (for example, hexyl), di(fluoroalkyl)siloxane units, (fluoroalkyl)(methyl)siloxane units, and (fluoroalkyl)(phenyl)siloxane units wherein each fluoroalkyl group is independently selected from fluoroalkyl groups having 3 to about 8 carbon atoms (for example, trifluoropropyl or nonafluorohexyl), diphenylsiloxane units, and combinations thereof. Although homopolymer is often preferred, copolymers can be preferred for some applications.

The polysiloxanes useful as component (b) can be used in the curable composition of the invention singly or in the form of mixtures of different polysiloxanes. The polysiloxanes can be prepared by known synthetic methods and many are commercially available. For example, Syl-Off™ Q2-7560 crosslinker, Syl-Off™ 7678 crosslinker, and the hydrosilyl-functional component (for example, Syl-Off™ 7048 crosslinker) of Syl-Off™ 292 and Syl-Off™ 294 coating compositions (all available from Dow Corning Corporation, Midland, Mich.) are preferred polysiloxanes, and other useful polysiloxane crosslinkers of varying molecular weight can be obtained from Gelest, Inc., Morrisville, Pa. (see, for example, the polysiloxanes described in Silicon Compounds: Silanes and Silicones, Second Edition, edited by B. Arkles and G. Larson, Gelest, Inc. (2008)).

Component (c)

Bases suitable for use as component (c) of the curable composition of the invention include amidines, guanidines (including substituted guanidines such as biguanides), phosphazenes, proazaphosphatranes (also known as Verkade's bases), and combinations thereof. Self-protonatable forms of the bases (for example, aminoacids such as arginine) generally are less suitable and therefore excluded, as such forms are self-neutralized. Preferred bases include amidines, guanidines, and combinations thereof (more preferably, amidines and combinations thereof most preferably, cyclic amidines and combinations thereof).

It has been discovered that the bases of the listed structural classes can effectively catalyze reaction between components (a) and (b), as described above. The bases can be used in the curable composition singly (individually) or in the form of mixtures of one or more different bases (including bases from different structural classes). If desired, the base(s) can be present in photolatent form (for example, in the form of an activatable composition that, upon exposure to radiation or heat, generates the base(s) in situ).

Useful amidines include those that can be represented by the following general formula:

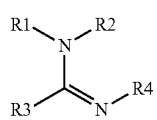

(III)

wherein R1, R2, R3, and R4 are each independently selected from hydrogen, monovalent organic groups, monovalent heteroorganic groups (for example, comprising nitrogen, oxygen, phosphorus, or sulfur in the form of groups or moieties that are bonded through a carbon atom and that do not contain acid functionality such as carboxylic or sulfonic), and combinations thereof and wherein any two or more of R1, R2, R3, and R4 optionally can be bonded together to form a ring structure (preferably, a five-, six-, or seven-membered ring; more preferably, a six- or seven-membered ring). The organic and heteroorganic groups preferably have from 1 to about 20 carbon atoms (more preferably, from 1 to about 10 carbon atoms; most preferably, from 1 to about 6 carbon atoms). Preferably, R4 is not hydrogen.

Amidines comprising at least one ring structure (that is, cyclic amidines) are generally preferred. Cyclic amidines comprising two ring structures (that is, bicyclic amidines) are more preferred.

Representative examples of useful amidine compounds include 1,2-dimethyl-1,4,5,6-tetrahydropyrimidine, 1-ethyl-2-methyl-1,4,5,6-tetrahydropyrimidine, 1,2-diethyl-1,4,5,6-tetrahydropyrimidine, 1-n-propyl-2-methyl-1,4,5,6-tetrahydropyrimidine, 1-isopropyl-2-methyl-1,4,5,6-tetrahydropyrimidine, 1-ethyl-2-n-propyl-1,4,5,6-tetrahydropyrimidine, 1-ethyl-2-isopropyl-1,4,5,6-tetrahydropyrimidine, DBU (that is, 1,8-diazabicyclo[5.4.0]-7-undecene), DBN (that is, 1,5-diazabicyclo[4.3.0]-5-nonene), and the like, and combinations thereof. Preferred amidines include 1,2-dimethyl-1,4,5,6-tetrahydropyrimidine, DBU (that is, 1,8-diazabicyclo[5.4.0]-7-undecene), DBN (that is, 1,5-diazabicyclo[4.3.0]-5-nonene), and combinations thereof, with DBU, DBN, and combinations thereof being more preferred and DBU most preferred.

Useful guanidines include those that can be represented by the following general formula:

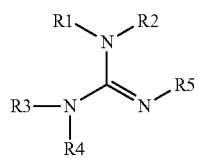

(IV)

wherein R1, R2, R3, R4, and R5 are each independently selected from hydrogen, monovalent organic groups, monovalent heteroorganic groups (for example, comprising nitrogen, oxygen, phosphorus, or sulfur in the form of groups or moieties that are bonded through a carbon atom and that do not contain acid functionality such as carboxylic or sulfonic), and combinations thereof; and wherein any two or more of R1, R2, R3, R4, and R5 optionally can be bonded together to form a ring structure (preferably, a five-, six-, or seven-membered ring; more preferably, a five- or six-membered ring; most preferably, a six-membered ring). The organic and heteroorganic groups preferably have from 1 to about 20 carbon atoms (more preferably, from 1 to about 10 carbon atoms; most preferably, from 1 to about 6 carbon atoms). Preferably, R5 is not hydrogen.

Guanidines comprising at least one ring structure (that is, cyclic guanidines) are generally preferred. Cyclic guanidines comprising two ring structures (that is, bicyclic guanidines) are more preferred.

Representative examples of useful guanidine compounds include 1-methylguanidine, 1-n-butylguanidine, 1,1-dimethylguanidine, 1,1-diethylguanidine, 1,1,2-trimethylguanidine, 1,2,3-trimethylguanidine, 1,3-diphenylguanidine, 1,1,2,3,3-pentamethylguanidine, 2-ethyl-1,1,3,3-tetramethylguanidine, 1,1,3,3-tetramethyl-2-n-propylguanidine, 1,1,3,3-tetramethyl-2-isopropylguanidine, 2-n-butyl-1,1,3,3-tetramethylguanidine, 2-tert-butyl-1,1,3,3-tetramethylguanidine, 1,2,3-tricyclohexylguanidine, TBD (that is, 1,5,7-triazabicyclo[4.4.0]dec-5-ene), MTBD (that is, 7-methyl-1,5,7-triazabicyclo[4.4.0]dec-5-ene), 7-ethyl-1,5,7-triazabicyclo[4.4.0]dec-5-ene, 7-n-propyl-1,5,7-triazabicyclo[4.4.0]dec-5-ene, 7-isopropyl-1,5,7-triazabicyclo[4.4.0]dec-5-ene, 7-n-butyl-1,5,7-triazabicyclo[4.4.0]dec-5-ene, 7-isobutyl-1,5,7-triazabicyclo[4.4.0]dec-5-ene, 7-tert-butyl-1,5,7-triazabicyclo[4.4.0]dec-5-ene, 7-cyclohexyl-1,5,7-triazabicyclo[4.4.0]dec-5-ene, 7-n-octyl-1,5,7-triazabicyclo[4.4.0]dec-5-ene, 7-2-ethylhexyl-1,5,7-triazabicyclo[4.4.0]dec-5-ene, 7-decyl-1,5,7-triazabicyclo[4.4.0]dec-5-ene, biguanide, 1-methylbiguanide, 1-n-butylbiguanide, 1-(2-ethylhexyl)biguanide, 1-n-octadecylbiguanide, 1,1-dimethylbiguanide, 1,1-diethylbiguanide, 1-cyclohexylbiguanide, 1-allylbiguanide, 1-n-butyl-N2-ethylbiguanide, 1,1'-ethylenebisguanide, 1-[3-(diethylamino)propyl]biguanide, 1-[3-(dibutylamino)propyl]biguanide, N',N'''-dihexyl-3,12-diimino-2,4,11,13-tetraazatetradecanediamidine, and the like, and combinations thereof. Preferred guanidines include TBD (that is, 1,5,7-triazabicyclo[4.4.0]dec-5-ene), MTBD (that is, 7-methyl-1,5,7-triazabicyclo[4.4.0]dec-5-ene), 2-tert-butyl-1,1,3,3-tetramethylguanidine, and combinations thereof. More preferred are TBD, MTBD, and combinations thereof.

If desired, the amidines and guanidines can be selected from those exhibiting a pH value lower than 13.4 when measured according to JIS Z 8802 (for example, 1,3-diphenylguanidine, DBU, DBN, or a combination thereof; preferably, DBU, DBN, or a combination thereof). The referenced method for determining the pH of aqueous solutions, JIS Z 8802, is carried out by first preparing an aqueous solution of base by adding 5 millimoles of base to 100 g of a mixed solvent composed of isopropyl alcohol and water in a weight ratio of 10:3. The pH of the resulting solution is then measured at 23° C. using a pH meter (for example, a Horiba Seisakusho Model F-22 pH meter).

Useful phosphazenes include those that can be represented by the following general formula:

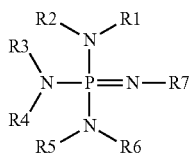

(V)

wherein R1, R2, R3, R4, R5, R6, and R7 are each independently selected from hydrogen, monovalent organic groups, monovalent heteroorganic groups (for example, comprising nitrogen, oxygen, phosphorus, or sulfur in the form of groups or moieties that are bonded through a carbon atom and that do not contain acid functionality such as carboxylic or sulfonic), and combinations thereof; and wherein any two or more of R1, R2, R3, R4, R5, R6, and R7 optionally can be bonded together to form a ring structure (preferably, a five-, six-, or seven-membered ring; more preferably, a five- or six-membered ring; most preferably, a six-membered ring). The organic and heteroorganic groups preferably have from 1 to about 20 carbon atoms (more preferably, from 1 to about 10 carbon atoms; most preferably, from 1 to about 6 carbon atoms). Preferably, R7 is not hydrogen.

Representative examples of useful phosphazene compounds include

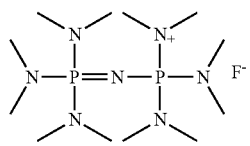

1,1,1,3,3,3-
hexakis(dimethylamino)
diphosphazenium fluoride

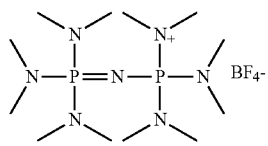

1,1,1,3,3,3-
hexakis(dimethylamino)
diphosphazenium
tetrafluoroborate

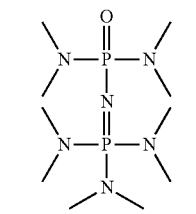

1,1,3,3,3-
pentakis(dimethylamino)-
$1\lambda^5, 3\lambda^5$-
diphosphazene
1-oxide

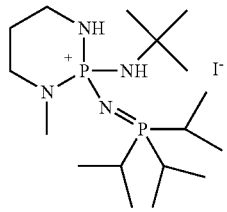

2-tert-butylamino-1-methyl-2-
[tris(dimethylamino)
phosphoranylidenamino]-
perhydro-1,3,2-
diazaphosphorinium iodide

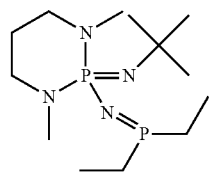

2-tert-butylimino-2-
diethylamino-1,3-
dimethylperhydro-1,3,2-
diazaphosphorine

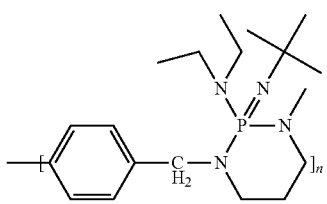

2-tert-butylimino-2-diethylamino-1,3-
diemethylperhydro-1,3,2-diazaphosphorine n = 2

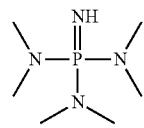

imino-
tris(dimethylamino)
phosphorane

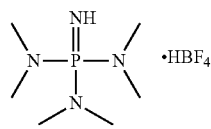

iminotris(dimethylamino)
phosphonium
tetrafluoroborate salt

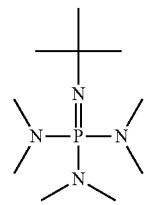

phosphazene base
$P_1$-t-Bu

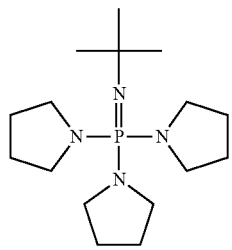
phosphazene base
P$_1$-t-Bu-
tris(tetramethylene)
purum
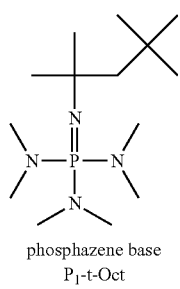
phosphazene base
P$_1$-t-Oct
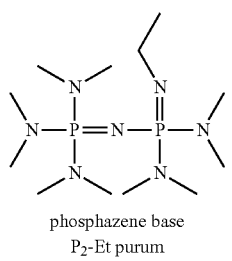
phosphazene base
P$_2$-Et purum
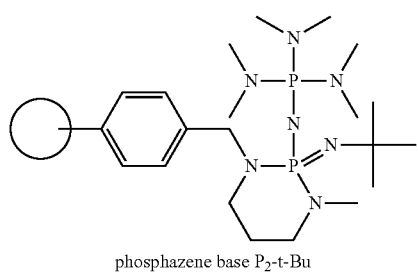
phosphazene base P$_2$-t-Bu
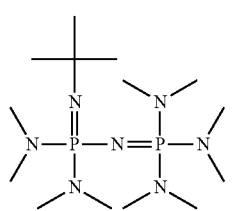
phosphazene base
P$_2$-t-Bu
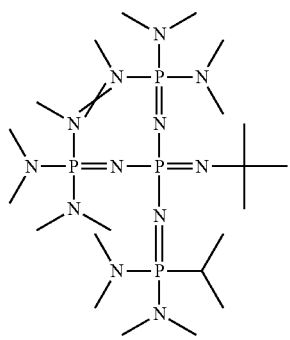
phosphazene base
P$_4$-t-Bu
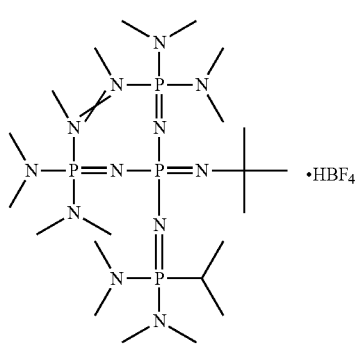
phosphazene base
P$_4$-t-Bu
tetrafluoroborate salt
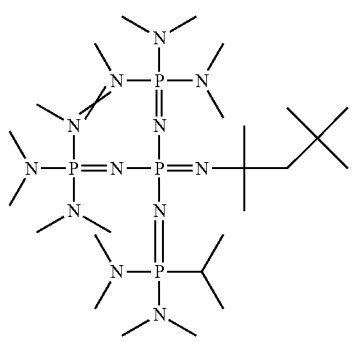
phosphazene base
P$_4$-t-Oct
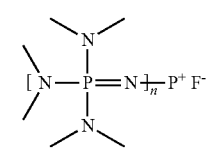
tetrakis[tris(dimethylamino)
phosphoranylidenamino]
phosphomium fluoride
n = 4

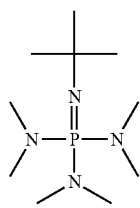

tert-butylimino-
tris(dimethylamino)
phosphorane

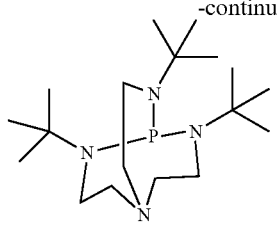

2,8,9-triisobutyl-
2,5,8,9-tetraaza-1-
phosphabicyclo
[3.3.3]undecane and the like, and combinations thereof. Preferred phosphazenes include 2-tert-butylimino-2-diethylamino-1,3-dimethylperhydro-1,3,2-diazaphosphorine, phosphazene base $P_1$-t-Bu-tris(tetramethylene), phosphazene base $P_4$-t-Bu, and combinations thereof.

Useful proazaphosphatrane bases (Verkade's bases) include those that can be represented by the following general formula:

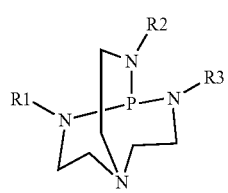

(VI)

wherein R1, R2, and R3 are each independently selected from hydrogen, monovalent organic groups, monovalent heteroorganic groups (for example, comprising nitrogen, oxygen, phosphorus, or sulfur in the form of groups or moieties that are bonded through a carbon atom and that do not contain acid functionality such as carboxylic or sulfonic), and combinations thereof (less preferably hydrogen). The organic and heteroorganic groups preferably have from 1 to about 20 carbon atoms (more preferably, from 1 to about 10 carbon atoms; most preferably, from 1 to about 6 carbon atoms).

Representative examples of useful proazaphosphatrane compounds include

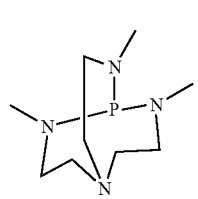

2,8,9-trimethyl-2,5,8,9-
tetraaza-1-
phosphabicyclo
[3.3.3]undecane

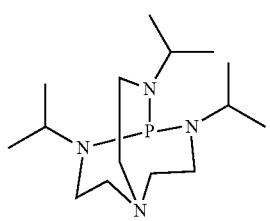

2,8,9-triisopropyl-
2,5,8,9-tetraaza-1-phosphabicyclo
[3.3.3]undecane and the like, and combinations thereof 2,8,9-triisopropyl-2,5,8,9-tetraaza-1-phosphabicyclo[3.3.3]undecane is a preferred proazaphosphatrane compound.

Preparation of Curable Composition

The curable composition of the invention can be prepared by combining components (a), (b), and (c) in essentially any order (preferably, with agitation or stirring). Preferably, components (a) and (b) are combined initially, followed by addition of component (c). The composition can be maintained as a relatively shelf-stable, 2-part system (for example, by keeping component (c) separate from the other two components), if desired, but a 1-part system (comprising all three components) can also be stable for periods of up to, for example, about two weeks in dry solvent (a relatively long pot life), prior to coating or other application of the composition.

The relative amounts of components (a) and (b) can vary widely, depending upon their nature and the desired properties of the curable and/or cured composition. Although stoichiometry prescribes a 1:1 molar ratio of reactive silane functionality (for example, one mole of hydrosilyl moieties for every mole of hydroxysilyl moieties), in practice it can be useful to have a deficiency or an excess of hydrosilyl functionality (for example, this can be useful when cure inhibitors are present). Molar ratios (of hydrosilyl moieties to hydroxysilyl moieties) up to, for example, about 8:1 or about 13:1 or even as high as about 35:1 can be useful. Component (c) (the base catalyst(s)) can be present in the curable composition in amounts ranging from about 0.1 to about 10 weight percent (preferably, from about 0.1 to about 5 weight percent; more preferably, from about 0.5 to about 2 weight percent), based upon the total weight of components (a), (b), and (c).

Preferably, the curable composition comprises at least one solvent or diluent to aid in storage stability, mixing, and/or coating, particularly when components (a) and (b) are polymeric. Suitable solvents for use in the curable composition of the invention include aprotic solvents such as aromatic solvents (for example, xylene, toluene, 1,2-dichlorobenzene, 1,3-dichlorobenzene, 1,4-dichlorobenzene, and the like, and mixtures thereof), ketones (for example, methyl ethyl ketone (MEK), cyclohexanone, and the like, and mixtures thereof), alkyl esters (for example, ethyl acetate, butyl acetate, and the like, and mixtures thereof), alkanes (for example, heptane, isoparaffinic hydrocarbons, and the like, and mixtures thereof), ethers (for example, t-butyl methyl ether, tetrahydrofuran (THF), and the like, and mixtures thereof), and the like, and mixtures thereof. Preferred solvents include aromatic solvents, alkanes, ketones, and mixtures thereof; with xylene, heptane, methyl ethyl ketone, and mixtures thereof being more preferred and heptane, methyl ethyl ketone, and mixtures thereof most preferred.

Minor amounts of optional components can be added to the curable composition to impart particular desired properties for particular curing methods or uses. Useful compositions can comprise conventional additives such as, for example, catalysts (including conventional condensation catalysts such as tin catalysts, which can be added as co-catalysts if desired), initiators, emulsifiers (including surfactants), stabilizers, anti-oxidants, flame retardants, adhesion promoters, release modifiers (for example, silicate MQ resin), colorants, thickeners (for example, carboxy methyl cellulose (CMC), polyvinylacrylamide, polypropylene oxide, polyethylene oxide/polypropylene oxide copolymers, polyalkenols), and the like, and mixtures thereof.

If desired, the curable composition can be prepared in the form of an emulsion (for example, by using water as a diluent). Useful emulsifiers (also known as emulgents) include surface active substances or surfactants. Silicone emulsions often contain water, silicone oil, stabilizing surfactants, preservatives, and other additives for viscosity stabilization and freeze-thaw stability.

The curable composition of the invention can be prepared in the form of an emulsion by any of a variety of known or hereafter-developed mechanical or chemical emulsification techniques. Some suitable emulsions are also commercially available (for example, Syl-Off™ 1181 aqueous emulsion coating composition, available from Dow Corning Corporation, Midland, Mich.) and can be used in combination with base catalyst (component (c)). Useful emulsification techniques include those described, for example, in European Patent Applications Nos. 0 268 982 (Toray Silicone Company, Ltd.), 0 459 500 (Dow Corning Corporation), and 0 698 633 (Dow Corning Corporation), the descriptions of the techniques being incorporated herein by reference.

A particularly useful technique for producing silicone in water emulsions is that described in U.S. Pat. No. 6,013,682 (Dalle et al.), the technique description being incorporated herein by reference. This technique provides emulsions in which silicones polymerize by chain extension at the interior of silicone droplets suspended in water. U.S. Pat. No. 5,229,212 (Reed) describes another useful technique in which a high molecular weight, water-soluble or water-dispersible polymeric thickening agent (such as polyethylene oxide) is utilized, the description of the technique being incorporated herein by reference.

Suitable emulsifiers for use in the curable composition of the invention include non-ionic (including polymeric non-ionic surfactants (for example, alkylpolysaccharide)), cationic, anionic, and amphoteric surfactants, and the like, and combinations thereof. The surfactants can be used individually or in combination. Although essentially any type of surfactant can be used, non-ionic surfactants can be preferred.

Useful non-ionic surfactants include those that are rendered hydrophilic by the presence of a polyethylene glycol chain (obtained by the polycondensation of ethylene oxide). Such non-ionic surfactants are termed "polyethoxylated non-ionics." Other examples of useful non-ionic surfactants include polyalkenols (also known as polyvinyl alcohols), polyoxyalkylene alkyl ethers, polyoxyalkylene sorbitan alkyl esters, polyoxyalkylene alkyl esters, polyoxyalkylene alkylphenol ethers, polyethylene glycols, polypropylene glycols, diethylene glycols, polyethylene oxide-polypropylene oxide block copolymers, ethoxylated or sulfonated resins, carboxymethyl cellulose and other polysaccharide derivatives, polyacrylates, xanthane, and the like, and combinations thereof. Preferred non-ionic surfactants include polymeric non-ionic surfactants and combinations thereof (more preferably, polyalkenols and combinations thereof).

Examples of useful cationic surfactants include quaternary ammonium hydroxides (for example, tetramethylammonium hydroxide, octyltrimethylammonium hydroxide, dodecyltrimethylammonium hydroxide, hexadecyltrimethylammonium hydroxide, octyldimethylbenzylammonium hydroxide, decyldimethylbenzyl ammonium hydroxide, didodecyldimethylbenzyl ammonium hydroxide, dioctadecyldimethylammonium hydroxide, tallow trimethylammonium hydroxide, cocotrimethylammonium hydroxide, and the like, and combinations thereof), corresponding salts of the quaternary ammonium hydroxides, fatty acid amines and amides and their derivatives, salts of the fatty acid amines and amides (including aliphatic fatty amines and amides) and their derivatives, homologs of aromatic amines having fatty chains, fatty amides derived from aliphatic diamines, fatty amides derived from disubstituted amines, derivatives of ethylene diamine, amide derivatives of amino alcohols, amine salts of long-chain fatty acids, quaternary ammonium bases derived from fatty amides of disubstituted diamines, quaternary ammonium bases of benzimidazolines, basic compounds of pyridinium and its derivatives, sulfonium compounds, quaternary ammonium compounds of betaine, urethanes of ethylene diamine, polyethylene diamines, polypropanolpolyethanol amines, and the like, and combinations thereof.

Examples of useful anionic surfactants include alkylbenzene sulfonates (detergents), fatty acids (soaps), alkyl sulfates such as lauryl sulfate (foaming agents), di-alkyl sulfosuccinates (wetting agents), lignosulfonates (dispersants), and the like, and combinations thereof. Other useful anionic surfactants include those described in U.S. Pat. No. 6,013,682 (Dalle et al.), the descriptions thereof being incorporated herein by reference.

Another class of useful surfactants is that of amphoteric or zwitterionic surfactants, which include single surfactant molecules that exhibit both anionic and cationic dissociations. Examples of useful amphoteric surfactants include betaines, sulfobetaines, natural substances such as aminoacids and phospholipids, and the like, and combinations thereof.

The amount of surfactant that can be included in the curable composition of the invention will vary (for example, depending upon the nature of the surfactant(s)). Amounts of surfactant in the range of about 0.01 to about 35 weight percent (based upon the total weight of the curable composition), however, can often be useful (with amounts in the range of about 0.1 to about 20 weight percent being preferred, and amounts in the range of about 0.5 to about 5 or 10 weight percent being more preferred). The total amount of water that can be included in the curable composition to form an aqueous emulsion can also vary but generally can be in the range of about 20 to about 95 weight percent (based upon the total weight of the curable composition).

If desired, the base catalyst (component (c)) can be pre-emulsified (for example, by addition of base catalyst to an aqueous solution of surfactant and/or thickening agent, followed by shaking or agitation of the resulting mixture) prior to its combination with the other components of the curable composition.

Use and Curing of Curable Composition

The curable composition of the invention can be used in various different applications. For example, the composition(s) can be used as sealants, release coatings, surface treatments, hardcoats, and the like. When used as fluorinated surface treatments, a degree of hydrophobicity and/or oleophobicity can be imparted to a variety of substrates (for example, for surface protection or to enhance ease of cleaning).

The curable composition of the invention (or, alternatively, its components) can be applied to at least a portion of at least one major surface of a substrate (for example, a sheet, a fiber, or a shaped object) by essentially any known or hereafter-developed application method, so as to form a variety of different coated articles. The composition can be applied in essentially any manner (and with essentially any thickness) that can form a useful coating.

Useful application methods include coating methods such as dip coating, spin coating, spray coating, wiping, roll coating, wire coating, and the like, and combinations thereof. The composition can be applied in neat form or in the form of solvent solutions (for example, in solvents such as alkyl esters, ketones, alkanes, aromatics, and the like, and mixtures thereof) or emulsions. When solvent is used, useful concentrations of the composition can vary over a wide range (for example, from about 1 to about 90 weight percent), depending upon the viscosity of the composition, the application method utilized, the nature of the substrate, and the desired properties.

Substrates suitable for use in preparing the coated articles include those having at least one surface comprising a material that is solid and preferably substantially inert to any coating or application solvent that is used. Preferably, the curable composition can adhere to the substrate surface through chemical interactions, physical interactions, or a combination thereof (more preferably, a combination thereof).

Suitable substrates can comprise a single material or a combination of different materials and can be homogeneous or heterogeneous in nature. Useful heterogeneous substrates include coated substrates comprising a coating of a material (for example, a metal or a primer) borne on a physical support (for example, a polymeric film).

Useful substrates include those that comprise wood, glass, minerals (for example, both man-made ceramics such as concrete and naturally-occurring stones such as marble and the like), polymers (for example, polycarbonate, polyester, polyacrylate, and the like) including multi-layer polymeric films, metals (for example, copper, silver, gold, aluminum, iron, stainless steel, nickel, zinc, and the like), metal alloys, metal compounds (for example, metal oxides and the like), leather, parchment, paper, textiles, painted surfaces, and combinations thereof. Preferred substrates include glass, minerals, wood, metals, metal alloys, metal compounds, polymers, and combinations thereof (more preferably, metals, metal alloys, metal compounds, polymers, and combinations thereof).

Preferred substrates include those used for pressure-sensitive adhesive (PSA) products. For example, the curable composition can be applied to suitable flexible or inflexible backing materials and then cured. Useful flexible backing materials include paper, Kraft paper, polyolefin-coated paper, plastic films (for example, poly(propylene), poly(ethylene), poly(vinyl chloride), polyester (including poly(ethylene terephthalate), polyamide, cellulose acetate, and ethyl cellulose), and the like, and combinations thereof, although essentially any surface requiring release toward adhesives can be utilized. Backings can thus also be of woven fabric formed of threads of synthetic or natural materials such as cotton, nylon, rayon, glass, or ceramic material, or they can be of nonwoven fabric such as air-laid webs of natural or synthetic fibers or blends of these. In addition, suitable backings can be formed of metal, metallized polymeric film, or ceramic sheet material. Primers (including surface treatments such as corona treatment) can be utilized, but they are not always necessary.

The curable composition of the invention can provide coatings that are suitable for use in the manufacture of PSA-coated labels and tapes. The specific level of release provided upon curing can be controllably varied through variation in, for example, the weight percentage and molecular weight of component (a) of the composition, or through the addition of release modifiers (for example, silicate MQ resin), which also can be varied in nature and/or amount.

The curable composition can be cured by concentration (for example, by allowing solvent evaporation). The preferred curing conditions will vary, depending upon the particular application and its accompanying requirements and conditions. Moisture can be present but generally is not necessary. Cure generally can be effected at temperatures ranging from room temperature (for example, about 20-23° C.) up to about 150° C. or more (preferably, temperatures of about 20° C. to about 125° C.; more preferably, about 20° C. to about 100° C.; most preferably, about 20° C. to about 80° C.). Curing times can range from a few minutes (for example, at room temperature) to hours (for example, under low catalyst conditions).

Release coatings obtained via cure of the curable composition of the invention generally contain little or no free silicone to adversely affect the tack and peel properties of PSAs that come in contact with them. The curable composition of the invention can cure relatively rapidly to provide relatively firmly anchored, highly crosslinked, solvent-resistant, tack-free coatings, which can be used with a broad range of PSA types (for example, acrylates, tackified natural rubbers, and tackified synthetic elastomers).

Articles in the form of PSA laminates (for example, comprising a layer of PSA borne on a release liner) can be prepared by placing a PSA layer in contact with the release coating through dry lamination, wet solution casting, or even by application of a photopolymerizable composition to the release coating, followed by irradiation to effect photopolymerization (for example, as described in U.S. Pat. No. 4,181, 752 (Martens et al.), the description of which is incorporated herein by reference). Such articles can exhibit relatively good storage stability (as evidenced, for example, by the results of room temperature and/or heat accelerated aging tests to evaluate any change in the level of release (peel force) from the release coating and/or in the subsequent level of adhesion to a desired substrate).

EXAMPLES

Objects and advantages of this invention are further illustrated by the following examples, but the particular materials and amounts thereof recited in these examples, as well as other conditions and details, should not be construed to unduly limit this invention. These examples are merely for illustrative purposes only and are not meant to be limiting on the scope of the appended claims.

Materials

Unless otherwise noted, all parts, percentages, ratios, etc., in the examples and in the remainder of the specification are by weight. Unless otherwise noted, all chemicals were obtained from, or are available from, chemical suppliers such as Aldrich Chemical Company, Milwaukee, Wis.

Test Method for Measuring Aged Release and Subsequent Adhesion

These tests measured the effectiveness of release liners that had been aged for a period of time at a constant temperature and relative humidity. The aged release value is a quantitative measure of the force required to remove a flexible adhesive tape from the release liner at a specific angle and rate of removal. This force is expressed in Newtons per decimeter (N/dm). Unless otherwise noted, one of the following four adhesive tapes was used to measure the aged release value and the subsequent adhesion (sometimes called readhesion) to a substrate.

Tape A is a pressure-activated, repositionable adhesive tape comprising a vinyl backing commercially available from 3M Company, St. Paul, Minn. under the trade designation 3M™ Controltac™ Graphic Film IJ180-10.

Tape B is a pressure-sensitive adhesive tape comprising a vinyl backing commercially available from 3M Company, St. Paul, Minn. under the trade designation 3M™ Scotchcal™ ElectroCut™ Graphic Film Series 7725.

Tape C is an acrylic pressure-sensitive adhesive tape comprising a polypropylene backing commercially available from 3M Company, St. Paul, Minn. under the trade designation Scotch™ Magic™ Tape 810.

Tape D is an acrylic pressure-sensitive adhesive tape comprising a polypropylene backing commercially available from 3M Company, St. Paul, Minn. under the trade designation Scotch™ Book Tape 845.

Release liners (release-coated substrates) of the invention were tested for their aged release values by lamination of one of the above-described adhesive tapes, with the release coating of the release liner facing the adhesive-bearing side of the tape. The resulting laminates were cut into test strips about 2.54 cm wide and approximately 12 cm long (or approximately 15 cm long for Examples 22-26 and Comparative Examples C-13-C-15). The test strips were then aged for a period of time at a constant temperature and relative humidity (RH), as specified in the various examples below. The aged test strips were attached to the working platen of a slip/peel tester (Model SP2000, obtained from Instrumentors, Inc., Strongsville, Ohio) using a 2.54 cm wide double-coated adhesive paper tape (commercially available from 3M Company, St. Paul, Minn. under the trade designation 3M™ Double Coated Paper Tape 410B) applied to the release liner side of the test strip. The attached test strip was rolled once on the working platen with a 2 kg rubber roller. The adhesive tape of the test strip was then removed from the release liner by peeling at 180 degrees and a rate of 2.3 meters per minute (90 inches per minute), and the force required for removing the adhesive tape from the release liner was measured over a five-second data collection time.

In an alternate version of the aged release test (used for Example 21, as indicated below), the test strips were attached to the working platen of the slip/peel tester using the double-coated adhesive paper tape applied to the adhesive tape side of the test strip. The attached test strip was rolled once on the working platen with a 2 kg rubber roller. The release liner of the test strip was then removed from the adhesive tape by peeling at 180 degrees and a rate of 2.3 meters per minute (90 inches per minute), and the force required for removing the release liner from the adhesive tape was measured over a five-second data collection time.

All release tests were carried out in a facility at constant temperature (23° C.) and constant relative humidity (50 percent). At least two measurements were made for each example, and the data are reported as an average of all measurements. Measurements were made in grams-force/inch and converted to N/dm.

After peeling of the adhesive tape from the release liner, the subsequent (180 degree peel) adhesion of the adhesive tape was measured by adhering the freshly peeled adhesive tape (without the release liner) to a float glass test panel, with the adhesive-bearing side of the tape in contact with the panel. The adhered adhesive tape was rubbed down on the test panel, first using light thumb pressure and then with a 2 kg rubber roller at a rate of 61 cm per minute. The subsequent adhesion value of the tape was then measured using the above-described instrument and test parameters. These measurements were taken to determine whether a drop in adhesion value occurred due to undesirable contamination of the adhesive surface by the release coating of the release liner. The subsequent adhesion test was also carried out at 23° C. and 50 percent relative humidity. At least two measurements were made for each example, and the data are reported as an average of all measurements. Measurements were made in grams-force/inch (or ounces-force/inch for Examples 22-26 and Comparative Examples C-13-C-15) and converted to N/dm.

Examples 1-10 and Comparative Examples C-1-C-12

A sample of a 30 weight percent solids dispersion of a blend of reactive hydroxysilyl-functional siloxane polymer(s) (said to comprise hydroxyl-terminated polydimethylsiloxane) and hydrosilyl-functional polysiloxane crosslinker (said to comprise poly(methyl)(hydrogen)siloxane) in xylene (a premium release coating composition obtained from Dow Corning Corporation, Midland, Mich., under the trade designation Syl-Off™ 292) was diluted to 10 weight percent solids with heptane. For each of Examples 1-10 and Comparative Examples C-1-C-12, 0.02 g of catalyst (listed in Table 1 below; all catalysts were obtained from Aldrich Chemical Company, Milwaukee, Wis.) was added to 5 g of Syl-Off™ 292 solution (10 weight percent in heptane) and then mixed. The resulting mixtures were coated on the primed side of a 50 micrometer thick polyester terephthalate (PET) film (obtained from Mitsubishi Polyester Film, Greer, S.C., under the trade designation Hostaphan™ 3SAB, referred to hereinafter as 3SAB PET film, which has one side chemically treated or primed to improve the adhesion of silicone coatings) using a number 4 rod. The resulting coated 3SAB PET samples were set aside at room temperature (about 23° C.) and their curing status (level of tackiness) was monitored. A coated sample was deemed cured if the coating solidified within 5 minutes. A coated sample was deemed not cured if the coating did not solidify and remained tacky for at least 24 hours at room temperature. The results are shown in Table 1 below.

TABLE 1

| Example No. | Catalyst | Curing |
|---|---|---|
| 1 | DBU (1,8-Diazabicyclo[5.4.0]undec-7-ene) | Yes |
| 2 | DBN (1,5-Diazabicyclo[4.3.0]non-5-ene) | Yes |
| 3 | 1,2-Dimethyl-1,4,5,6-tetrahydropyrimidine | Yes |

TABLE 1-continued

| Example No. | Catalyst | Curing |
|---|---|---|
| 4 | TBD (1,5,7-Triazabicyclo[4.4.0]dec-5-ene) | Yes |
| 5 | MTBD (7-Methyl-1,5,7-triazabicyclo[4.4.0]dec-5-ene) | Yes |
| 6 | 2-tert-Butyl-1,1,3,3-tetramethylguanidine | Yes |
| 7 | Phosphazene base $P_1$-t-Bu-tris(tetramethylene) | Yes |
| 8 | Phosphazene base $P_4$-t-Bu solution (1M in Hexane) | Yes |
| 9 | 2-tert-Butylimino-2-diethylamino-1,3-dimethylperhydro-1,3,2-diazaphosphorine | Yes |
| 10 | 2,8,9-Triisopropyl-2,5,8,9-tetraaza-1-phosphabicyclo[3,3,3]undecane | Yes |
| C-1 | 1,1,3,3-Tetramethylguanidine | No |
| C-2 | N,N'-Diisopropylcarbodiimide | No |
| C-3 | N,N'-Diicyclohexylcarbodiimide | No |
| C-4 | Imidazole | No |
| C-5 | N-Methylimidazole | No |
| C-6 | 1,2-Dimethylimidazole | No |

TABLE 1-continued

| Example No. | Catalyst | Curing |
|---|---|---|
| C-7 | 1,4-Diazabicyclo[2.2.2]octane | No |
| C-8 | 4,4'-Trimethylenebis(1-methylpiperidine) | No |
| C-9 | 2,6-Dimethylpyridine | No |
| C-10 | 4-Dimethylaminopyridine | No |
| C-11 | 2,2,6,6-Tetramethylpiperidine | No |
| C-12 | | No |

Example 11

9 g of Syl-Off™ 292 release coating composition, 0.1 g 1,8-diazabicyclo[5.4.0]-7-undecene (DBU, obtained from Aldrich Chemical Company, Milwaukee, Wis.), 16.7 g heptane, and 4.2 g methyl ethyl ketone (MEK) were weighed into a 120 mL glass jar. The glass jar was shaken until the contents were homogeneous. The homogeneous mixture was coated on the primed side of a 50 micrometers thick 3SAB PET film.

The coated film was taped to a cardboard and then left under ambient conditions (about 23° C.) for at least 3 minutes. After 2 minutes, the coating was not greasy but could be scuffed with a light finger rub. After 2 minutes and 40 seconds, the coating was firm and could not be scuffed with a finger rub. The coated film was then placed in a Despatch oven (Model RFD2-19-2E, commercially available from Despatch Industries, Minneapolis, Minn.) with the heat turned off and the fans turned on for 3 minutes in order to remove the solvents.

Example 12

29.4 g of Syl-Off™ 292 release coating composition, 0.1 g DBU, 56.4 g heptane, and 14.1 g MEK were weighed into a 120 mL glass jar. The glass jar was shaken until the contents were homogeneous. The homogeneous mixture was coated on the primed side of a 50 micrometers thick 3SAB PET film.

The coated film was taped to a cardboard and then left under ambient conditions (about 23° C.) for at least 3 minutes. After 1 minute and 30 seconds, the coating was dry and felt cured to the touch. The coated film was then placed in a Despatch oven with the heat turned off and the fans turned on for 3 minutes in order to remove the solvents.

Example 13

29.4 g of Syl-Off™ 292 release coating composition, 0.05 g DBU, 56.4 g heptane, and 14.1 g MEK were weighed into a 120 mL glass jar. The glass jar was shaken until the contents were homogeneous. The homogeneous mixture was coated on the primed side of a 50 micrometers thick 3SAB PET film.

The coated film was taped to a cardboard and then left under ambient conditions (about 23° C.) for at least 3 minutes. After 1 minute and 15 seconds, the coating was dry and felt cured to the touch. The coated film was then placed in a Despatch oven with the heat turned off and the fans turned on for 3 minutes in order to remove the solvents.

Example 14

0.1 g 2-tert-Butylimino-2-diethylamino-1,3-dimethylperhydro-1,3,2-diazaphosphorine (BEMP, obtained from Aldrich Chemical Company, Milwaukee, Wis.), 56.4 g heptane, 14.1 g MEK, and 29.4 g of Syl-Off™ 292 release coating composition were weighed into a 120 mL glass jar in the indicated order. The glass jar was shaken until the contents were homogeneous. The homogeneous mixture was coated on the primed side of a 50 micrometers thick 3SAB PET film.

The coated film was taped to a cardboard and then left under ambient conditions (about 23° C.) for at least 3 minutes. After 1 minute and 30 seconds, the coating was dry and felt cured to the touch. The coated film was then placed in a Despatch oven with the heat turned off and the fans turned on for 3 minutes in order to remove the solvents.

Example 15

0.05 g 2,8,9-Triisopropyl-2,5,8,9-tetraaza-1-phosphabicyclo[3.3.3]undecane (TTP, obtained from Aldrich Chemical Company, Milwaukee, Wis.), 56.45 g heptane, 14.1 g MEK, and 29.4 g of Syl-Off™ 292 release coating composition were weighed into a 240 mL glass jar. The glass jar was shaken until the contents were homogeneous. The homogeneous mixture was coated on the primed side of a 50 micrometers thick 3SAB PET film and left in the hood to air dry (at about 23° C.). The coated film was dry to the touch and anchored well within minutes.

Example 16

0.34 g of 100 percent active solids fluorofunctional silicone crosslinker (said to comprise greater than 60 weight percent trimethylsiloxy-terminated methyl(perfluorobutylethyl), methylhydrogen siloxane; obtained from Dow Corning Corporation, Midland, Mich., under the trade designation Syl-Off™ Q2-7560) and 0.8 g of hydroxyl-terminated polydimethylsiloxane (silanol-terminated PDMS, molecular weight (MW) of 400-700, obtained from Gelest, Inc., Morrisville, Pa., under the trade designation GELEST DMS-S12) and 8.86 g of heptane were mixed to prepare a 10 weight percent solids solution. 0.04 g of DBU catalyst was added to the solution. After mixing, the resulting fresh solution was coated on the primed side of a 50 micrometers thick 3SAB PET film. The coating was dried and cured at room temperature (about 23° C.; cured after about 6 minutes).

Example 17

The coating solution of Example 11 (comprising 3.3 weight percent DBU) was used for a bath life study. For this study, the viscosity of the coating solution was measured periodically using a viscometer (Model DV-II+ made by Brookfield Engineering Laboratories, Inc., Middleboro, Mass.) to determine if and/or when the solution would congeal. The solution was adversely affected 15 hours after solution preparation.

Example 18

The coating solutions of Examples 11, 12, and 13 were allowed to age at room temperature (about 23° C.), and, periodically (at 0, 1, 2, 4, and 6 hours of aging), each solution was coated on the primed side of a 50 micrometers thick 3SAB PET film. The cure time, defined as the elapsed time needed so that the coating could not be rubbed off by finger, was determined for each coating (for each coating solution and for each aging time). The resulting cure times are shown in Table 2 below.

TABLE 2

| Aging Time | Cure Time (minutes) | | |
|---|---|---|---|
| (hours) | Example 11 | Example 12 | Example 13 |
| 0 | 1.5 | 1.5 | 1.75 |
| 1 | 1.5 | 3 | 3.67 |
| 2 | 3.25 | 2 | 4 |
| 4 | 7 | 3 | 4.33 |
| 6 | 6 | 3.75 | 5 |

Example 19

The coating solutions of Examples 11-15 were coated on the primed sides of 50 micrometers thick 3SAB PET films, and the coatings were cured to form release liners. The release liners were then aged for 7 days at a relative humidity of 50 percent at 23° C. and 70° C., respectively. The aged release and subsequent adhesion values for the release liners were then determined by carrying out the above-described test method. The resulting data is shown in Table 3 below (as well as the data obtained for blank 3SAB PET films with no release coating).

TABLE 3

| Release Liner Example No. | Laminating Tape | Release (N/dm) (23° C.) | Release (N/dm) (70° C.) | Subsequent Adhesion (N/dm) (23° C.) | Subsequent Adhesion (N/dm) (70° C.) |
|---|---|---|---|---|---|
| 11 | Tape A | 0.42 | 0.43 | 63.52 | 56.73 |
| 12 | Tape A | 0.45 | 0.45 | 60.38 | 56.53 |
| 13 | Tape A | 0.47 | 0.72 | 62.07 | 54.67 |

TABLE 3-continued

| Release Liner Example No. | Laminating Tape | Release (N/dm) (23° C.) | Release (N/dm) (70° C.) | Subsequent Adhesion (N/dm) (23° C.) | Subsequent Adhesion (N/dm) (70° C.) |
|---|---|---|---|---|---|
| 14 | Tape A | 0.45 | 1.03 | 65.16 | 61.57 |
| 15 | Tape A | 0.52 | 1.18 | 63.74 | 55.81 |
| Blank Film | Tape A | 0.47 | 0.83 | 71.13 | 57.85 |
| 11 | Tape B | 0.39 | 0.43 | 70.20 | 63.30 |
| 12 | Tape B | 0.39 | 0.43 | 67.65 | 63.67 |
| 13 | Tape B | 0.42 | 0.65 | 67.77 | 62.22 |
| 14 | Tape B | 0.41 | 0.84 | 73.15 | 69.85 |
| 15 | Tape B | 0.53 | 1.10 | 68.17 | 65.68 |
| Blank Film | Tape B | 2.25 | 3.87 | 63.84 | 65.78 |
| 11 | Tape C | 0.19 | 0.27 | 24.07 | 23.26 |
| 12 | Tape C | 0.15 | 0.17 | 24.06 | 22.68 |
| 13 | Tape C | 0.16 | 0.27 | 26.34 | 21.87 |
| 14 | Tape C | 0.17 | 0.34 | 27.10 | 26.50 |
| 15 | Tape C | 0.25 | 0.48 | 22.51 | 16.21 |
| 11 | Tape D | 0.20 | 0.26 | 38.25 | 35.98 |
| 12 | Tape D | 0.20 | 0.21 | 37.44 | 40.21 |
| 13 | Tape D | 0.22 | 0.25 | 39.41 | 38.40 |
| 14 | Tape D | 0.21 | 0.28 | 46.90 | 42.58 |
| 15 | Tape D | 0.35 | 0.39 | 42.51 | 41.27 |

Example 20

The coating composition of Example 11 was coated on the primed side of a 50 micrometers thick 3SAB PET film, and the composition was cured to form a release liner. An acrylic radiation-sensitive syrup of liquid monomers (a mixture of 90 parts by weight isooctyl acrylate and 10 parts by weight acrylic acid; less than 10 percent polymerized; essentially as described in Examples 1-7 of U.S. Pat. No. 4,181,752 (Martens et al.), the description of which is incorporated herein by reference) was coated onto the release liner with a 25 micrometer thick PET film overlay (obtained from Mitsubishi Polyester Film, Greer, S.C.) using a notched bar coater to form a continuous web of acrylic syrup nominally 50 micrometer thick. The resulting coated web was then polymerized to more than 95 percent conversion by exposing the acrylic syrup to UV-A radiation with two 350BL lamps (available from Osram Sylvania, Danvers, Mass.) through the PET overlay in a nitrogen inert environment. Upon curing, the polymerized syrup formed a PET-backed pressure-sensitive adhesive (PSA) layer on the release liner. The resulting 3-layer construction of 25 micrometer PET film/50 micrometer PSA/PET release liner was release tested after cutting test sample strips of 2.54 cm wide by nominally 12 cm in length. The test sample strips were aged at a constant temperature of 23° C. and a constant relative humidity of 50 percent or in an oven set at 70° C. for a specified length of time prior to testing, as shown in Table 4 below. Release testing was carried out according to the above-described test method for measuring aged release, and the results are shown in Table 4.

TABLE 4

| Aging Conditions | Release (N/dm) |
|---|---|
| 8 days at 23° C., 50% RH | 0.89 |
| 21 days at 23° C., 50% RH | 1.21 |
| 7 days at 70° C. | 1.24 |

Example 21

The coating solution of Example 11 was coated on one side of a Polyethylene Coated Kraft paper (PCK, 156 grams per square meter weight, available from International Converter, Kaukauna, Wis.), and the resulting coating was cured to form a PCK release liner. An acrylic radiation-sensitive syrup (90 parts by weight isooctyl acrylate and 10 parts by weight acrylic acid; less than 10 percent polymerized) was coated onto the release liner with a 25 micrometer thick PET film overlay using a notched bar coater to form a continuous web of acrylic syrup nominally 50 micrometers thick. The resulting coated web was then polymerized to more than 95 percent conversion by exposing the acrylic syrup to UV-A radiation with two 350BL lamps through the 25 micrometer thick PET overlay and in a nitrogen inert environment. Upon curing, the polymerized syrup formed a PET-backed pressure-sensitive adhesive (PSA) layer on the release liner. The resulting 3-layer construction of 25 micrometer PET film/50 micrometer PSA/PCK release liner was prepared for release testing by cutting test sample strips of 2.54 cm wide by nominally 12 cm in length. The test sample strips were aged at a constant temperature of 23° C., 32° C., or 70° C. and a constant relative humidity of 50 percent, 90 percent, or without humidity control, for a specified length of time prior to testing, as shown in Table 5 below. Aged release testing was then carried out according to the above-described alternate aged release test method, wherein the PCK release liner was peeled from the PET-backed PSA. The resulting data is shown in Table 5 below.

TABLE 5

| Aging Conditions | Release (N/dm) |
|---|---|
| 7 days at 23° C. and 50% RH | 0.71 |
| 21 days at 23° C. and 50% RH | 1.07 |
| 3 days at 70° C. with no RH control | 0.39 |
| 7 days at 32° C. and 90% RH | 1.37 |

Emulsions

Examples 22-26 and Comparative Examples C-13-C-15

DBU-PVA Blend 6.0 g of polyvinyl alcohol NJE-249 (Kuraray America Inc., Houston, Tex.) and 54.0 g of deionized water were weighed into a 120 mL jar and left at room temperature (about 23° C.) overnight to give a viscous clear solution. To 5.0 g of this solution, 5.0 g of 1,8-diazabicyclo[5.4.0]undec-7-ene (DBU, available from Aldrich Chemical Company, Milwaukee, Wis.) was added, and the solution was shaken well to mix all the contents to give a homogeneous solution.

Example 22

10.0 g of SYL-OFF™ 1181 emulsion coating composition (a 40 weight percent solids aqueous emulsion of hydroxysilyl-functional siloxane polymer(s) (said to comprise hydroxyl-terminated polydimethylsiloxane), hydrosilyl-functional polysiloxane crosslinker (said to comprise poly(methyl)(hydrogen)siloxane), and vinyl alcohol polymer with vinyl acetate; available from Dow Corning Corporation, Midland, Mich.), 0.16 g of 1,8-diazabicyclo[5.4.0]undec-7-ene (DBU, available from Aldrich Chemical Company, Milwaukee, Wis.), and 29.84 g of deionized water were weighed into a 120 mL glass jar. The glass jar was shaken to mix all the contents well. The resulting solution had a milky appearance.

Release liners (release-coated substrates) of the invention were prepared using a two-sided 58# corona-treated polyolefin-coated kraft paper (available from Jen Coat Inc., P.O. Box 274, Westfield, Mass.) having a glossy side and a matte side as a coating substrate. The glossy side was coated with the release coating compositions of the invention using a number 4 wire wound rod (available from RD Specialties, Webster, N.Y.), which deposited approximately a 9.1 microns thick wet film on the coating substrate. The resulting coated polyolefin-coated kraft paper was then cured at room temperature (about 23° C.) for 8 hours or in an oven at 50° C. for 5 minutes.

The resulting cured release liner was tested for release and subsequent adhesion as described above using Tape D and aging for 7 days (23° C., 50% RH). The results are shown in Table 6 below.

Comparative Example C-13

10.0 g of SYL-OFF™ 1181 emulsion coating composition, 0.8 g SYL-OFF™ 1171A catalyst (a 50 weight percent solids aqueous emulsion of organotin catalyst (said to comprise dioctyl tin dilaurate); available from Dow Corning Corporation, Midland, Mich.), and 29.2 g of deionized water were weighed into a 120 mL glass jar. The glass jar was shaken to mix all the contents. The resulting solution had a milky appearance.

Release liners (release-coated substrates) were prepared using a two-sided 58# corona-treated polyolefin-coated kraft paper (available from Jen Coat Inc., P.O. Box 274, Westfield, Mass.) having a glossy side and a matte side as a coating substrate. The glossy side was coated with the release coating compositions of the invention using a number 4 wire wound rod (available from RD Specialties, Webster, N.Y.), which deposited approximately a 9.1 microns thick wet film on the coating substrate. The resulting coated polyolefin-coated kraft paper was then cured at room temperature (about 23° C.) for 8 hours or in an oven at 50° C. for 5 minutes.

The resulting cured release liner was tested for release and subsequent adhesion as described above using Tape D and aging for 7 days (23° C., 50% RH). The results are shown in Table 6 below.

Example 23

10.0 g of SYL-OFF™ 1181 emulsion coating composition, 29.84 g deionized water, and 0.16 g of DBU (1,8-diazabicyclo[5.4.0]undec-7-ene) were weighed into a 120 mL glass jar. The glass jar was shaken to mix all the contents well. The resulting solution had a milky appearance. The solution was coated on 50# clay-coated kraft (CCK) paper (Lumisil™ CCK, available from Stora Enso, Stamford, Conn.) with a number 4 wire wound rod. The resulting coated substrate was taped to a cardboard and cured in an oven at 50° C. for 5 minutes.

The resulting cured release liner was tested for release and subsequent adhesion as described above using Tape C and aging for 3 days (23° C., 50% RH). The results are shown in Table 6 below.

Example 24

10.0 g of SYL-OFF™ 1181 emulsion coating composition, 29.68 g deionized water, and 0.32 g of DBU-PVA blend catalyst (described above) were weighed into a 120 mL glass jar. The glass jar was shaken to mix all the contents well. The resulting solution had a milky appearance. The solution was coated on 50# clay-coated kraft (CCK) paper (Lumisil™ CCK, available from Stora Enso, Stamford, Conn.) with a number 4 wire wound rod. The resulting coated substrate was taped to a cardboard and cured in an oven at 50° C. for 5 minutes.

The resulting cured release liner was tested for release and subsequent adhesion as described above using Tape C and aging for 3 days (23° C., 50% RH). The results are shown in Table 6 below.

Comparative Example C-14

10.0 g of SYL-OFF™ 1181 emulsion coating composition, 29.2 g deionized water, and 0.8 g SYL-OFF™ 1171A catalyst were weighed into a 120 mL glass jar. The glass jar was shaken to mix all the contents well. The resulting solution had a milky appearance. The solution was coated on 50# clay-coated kraft (CCK) paper (Lumisil™ CCK, available from Stora Enso, Stamford, Conn.) with a number 4 wire wound rod. The resulting coated substrate was taped to a cardboard and cured in an oven at 50° C. for 5 minutes.

The resulting cured release liner was tested for release and subsequent adhesion as described above using Tape C and aging for 3 days (23° C., 50% RH). The results are shown in Table 6 below.

Example 25

10.0 g of SILCOLEASE™ PC-168 (Bluestar Silicones, East Brunswick, N.J.) release coating composition (believed to be an approximately 60 weight percent solids aqueous emulsion comprising hydroxysilyl-functional polydimethylsiloxane polymer and hydrosilyl-functional polysiloxane crosslinker (poly(methyl)(hydrogen)siloxane)), 29.84 g deionized water, and 0.16 g DBU catalyst were weighed into a 120 mL glass jar. The glass jar was shaken to mix all the contents well. The resulting solution had a milky appearance. The solution was coated on a supercalendared kraft (SCK) paper (RLS 320, available from Thilmany Pulp and Paper Co., Kaukauna, Wis.) with a number 4 wire wound rod. The resulting coated substrate was taped to a cardboard and cured in an oven at 50° C. for 5 minutes.

The resulting cured release liner was tested for release and subsequent adhesion as described above using Tape C and aging for 3 days (23° C., 50% RH). The results are shown in Table 6 below.

Example 26

10.0 g of SILCOLEASE™ PC-168 release coating composition, 29.68 g deionized water, and 0.32 g DBU-PVA blend catalyst (described above) were weighed into a 120 mL glass jar. The glass jar was shaken to mix all the contents well. The resulting solution had a milky appearance. The solution was coated on a supercalendared kraft (SCK) paper (RLS 320, available from Thilmany Pulp and Paper Co., Kaukauna, Wis.) with a number 4 wire wound rod. The resulting coated substrate was taped to a cardboard and cured in an oven at 50° C. for 5 minutes.

The resulting cured release liner was tested for release and subsequent adhesion as described above using Tape C (available from 3M Company, St. Paul, Minn.) and aging for 3 days (23° C., 50% RH). The results are shown in Table 6 below.

Comparative Example C-15

10.0 g of SILCOLEASE™ PC-168 release coating composition, 29.2 g deionized water, and 0.8 g SILCOLEASE™ PC-94 catalyst (said to be an aqueous emulsion comprising dioctyl tin dilaurate) were weighed into a 120 mL glass jar. The glass jar was shaken to mix all the contents well. The resulting solution had a milky appearance. The solution was coated on supercalendared kraft (SCK) paper (RLS 320, available from Thilmany Pulp and Paper Co., Kaukauna, Wis.) with a number 4 wire wound rod. The resulting coated substrate was taped to a cardboard and cured in an oven at 50° C. for 5 minutes.

The resulting cured release liner was tested for release and subsequent adhesion as described above using Tape C and aging for 3 days (23° C., 50% RH). The results are shown in Table 6 below.

TABLE 6

| Example No. | Curing Conditions | Aging Time (days at 23° C. and 50% RH) | Release (N/dm) | Subsequent Adhesion (N/dm) |
|---|---|---|---|---|
| 22 | 23° C.-8 hrs | 7 | 0.40 | 27.1 |
| 22 | 50° C.-5 min | 7 | 0.20 | 22.4 |
| C-13 | 23° C.-8 hrs | 7 | 0.24 | 28.1 |
| C-13 | 50° C.-5 min | 3 | 0.20 | 26.9 |
| 23 | 50° C.-5 min | 3 | 1.22 | 19.7 |
| 24 | 50° C.-5 min | 3 | 0.46 | 18.3 |
| C-14 | 50° C.-5 min | 3 | 0.82 | 26.8 |
| 25 | 50° C.-5 min | 3 | 0.75 | 18.3 |
| 26 | 50° C.-5 min | 3 | 1.47 | 20.0 |
| C-15 | 50° C.-5 min | 3 | 0.50 | 23.3 |

The referenced descriptions contained in the patents, patent documents, and publications cited herein are incorporated by reference in their entirety as if each were individually incorporated. Various unforeseeable modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only, with the scope of the invention intended to be limited only by the claims set forth herein as follows.

We claim:
1. A coating process comprising
    (a) providing a curable polysiloxane composition comprising
        (1) at least one polydiorganosiloxane, fluorinated polydiorganosiloxane, or combination thereof comprising reactive silane functionality comprising at least two hydroxysilyl moieties,
        (2) at least one polydiorganosiloxane, fluorinated polydiorganosiloxane, or combination thereof comprising reactive silane functionality comprising at least two hydrosilyl moieties, and
        (3) at least one base selected from amidines, guanidines, phosphazenes, proazaphosphatranes, and combinations thereof,
    wherein at least one of said components (1) and (2) has an average reactive silane functionality of at least three;
    (b) providing at least one substrate having at least one major surface;
    (c) applying said curable polysiloxane composition to at least a portion of at least one said major surface of said substrate; and
    (d) allowing or inducing said curable polysiloxane composition to cure to form a release coating.
2. The coating process of claim 1, wherein said components (1) and (2) of said curable polysiloxane composition each comprise at least one polydiorganosiloxane; and/or wherein said polydiorganosiloxane comprises polydimethylsiloxane.

3. The coating process of claim 1, wherein said component (1) of said curable polysiloxane composition is hydroxyl-endblocked.

4. The coating process of claim 1, wherein said component (1) of said curable polysiloxane composition is selected from polysiloxanes that are represented by the following general formula:

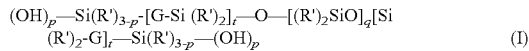
(OH)$_p$—Si(R')$_{3-p}$-[G-Si (R')$_2$]$_t$—O—[(R')$_2$SiO]$_q$[Si (R')$_2$-G]$_t$—Si(R')$_{3-p}$—(OH)$_p$     (I)

wherein each p is independently an integer of 1, 2, or 3; each G is independently a divalent linking group; each R' is independently selected from alkyl, alkenyl, fluoroalkyl, aryl, fluoroaryl, cycloalkyl, fluorocycloalkyl, heteroalkyl, heterofluoroalkyl, heteroaryl, heterofluoroaryl, heterocycloalkyl, heterofluorocycloalkyl, and combinations thereof; q is an integer of 0 to 15,000; and each t is independently an integer of 0 or 1.

5. The coating process of claim 4, wherein each said G is independently selected from oxy, alkylene, arylene, heteroalkylene, heteroarylene, cycloalkylene, heterocycloalkylene, and combinations thereof; each said R' is independently selected from alkyl, fluoroalkyl, aryl, and combinations thereof; said q is an integer of 20 to 15,000; and/or said t is an integer of 0.

6. The coating process of claim 1, wherein said component (1) of said curable polysiloxane composition comprises a mixture of (i) at least one polydiorganosiloxane, fluorinated polydiorganosiloxane, or combination thereof having a weight average molecular weight in the range of 300,000 to 1,000,000 and (ii) at least one polydiorganosiloxane, fluorinated polydiorganosiloxane, or combination thereof having a weight average molecular weight in the range of about 150 to about 150,000; and/or wherein said component (2) of said curable polysiloxane composition has an average reactive silane functionality of at least three.

7. The coating process of claim 1, wherein said component (2) of said curable polysiloxane composition is selected from polysiloxanes that are represented by the following general formula:

R'$_2$R"SiO(R'$_2$SiO)$_r$(HR'SiO)$_s$SiR"R'$_2$     (II)

wherein each R' is independently selected from alkyl, alkenyl, fluoroalkyl, aryl, fluoroaryl, cycloalkyl, fluorocycloalkyl, heteroalkyl, heterofluoroalkyl, heteroaryl, heterofluoroaryl, heterocycloalkyl, heterofluorocycloalkyl, and combinations thereof; each R" is independently hydrogen or R'; r is an integer of 0 to 150; and s is an integer of 2 to 150.

8. The coating process of claim 7, wherein each said R' is independently selected from alkyl, fluoroalkyl, aryl, and combinations thereof.

9. The coating process of claim 7, wherein said R' and said R" are methyl; said r is an integer of 0; and/or said s is an integer of 40.

10. The coating process of claim 1, wherein said component (3) of said curable polysiloxane composition is selected from (1) amidine compounds that are represented by the following general formula:

(2) guanidine compounds that are represented by the following general formula:

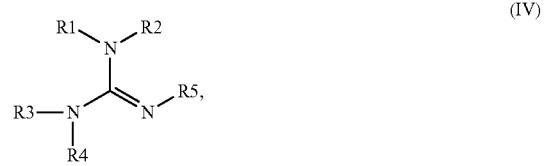

(3) phosphazene compounds that are represented by the following general formula:

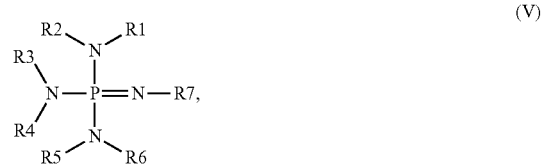

(4) proazaphosphatrane compounds that are represented by the following general formula:

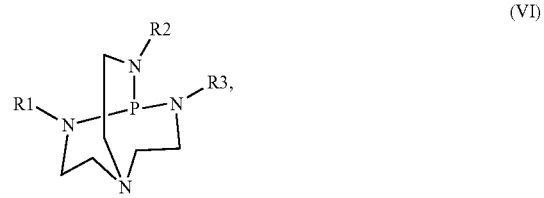

and combinations thereof;
wherein R1, R2, R3, R4, R5, R6, and R7 are each independently selected from hydrogen, monovalent organic groups, monovalent heteroorganic groups, and combinations thereof; and wherein any two or more of R1, R2, R3, R4, R5, R6, and R7 of said amidine, guanidine, and/or phosphazene compounds optionally can be bonded together to form a ring structure.

11. The coating process of claim 10, wherein said component (3) is selected from amidine compounds, guanidine compounds, phosphazene compounds, and combinations thereof that each comprise at least one said ring structure.

12. The coating process of claim 1, wherein said component (3) of said curable polysiloxane composition is selected from 1,2-dimethyl-1,4,5,6-tetrahydropyrimidine, 1,8-diazabicyclo[5.4.0]-7-undecene (DBU), 1,5-diazabicyclo[4.3.0]-5-nonene (DBN), 1,5,7-triazabicyclo[4.4.0]dec-5-ene (TBD), 7-methyl-1,5,7-triazabicyclo[4.4.0]dec-5-ene (MTBD), 2-tert-butyl-1,1,3,3-tetramethylguanidine, 2-tert-butylimino-2-diethylamino-1,3-dimethylperhydro-1,3,2-diazaphosphorine, phosphazene base P$_1$-t-Bu-tris(tetramethylene), phosphazene base P$_4$-t-Bu, 2,8,9-triisopropyl-2,5,8,9-tetraaza-1-phosphabicyclo[3.3.3]undecane, and combinations thereof.

13. The coating process of claim 1, wherein said base is selected from amidines, guanidines, and combinations thereof.

14. The coating process of claim 13, wherein said base is selected from amidines and combinations thereof.

15. The coating process of claim 14, wherein said amidine is selected from 1,8-diazabicyclo[5.4.0]-7-undecene (DBU), 1,5-diazabicyclo[4.3.0]-5-nonene (DBN), and combinations thereof.

16. The coating process of claim 1, wherein said curable polysiloxane composition is an organometallic catalyst-free composition; and/or wherein said curable polysiloxane composition is in the form of an emulsion.

17. An article comprising at least one substrate having at least one major surface, said substrate bearing, on at least a portion of at least one said major surface, a release coating prepared by the coating process of claim 1.

18. The article of claim 17, wherein said article further comprises a layer of pressure-sensitive adhesive prepared by application of a photopolymerizable composition to said release coating, followed by irradiation of said photopolymerizable composition to effect photopolymerization thereof.

19. The article of claim 17, wherein said article further comprises a layer of pressure-sensitive adhesive in contact with said release coating.

20. A coating process comprising
  (a) providing a curable polysiloxane composition comprising
    (1) at least one polydiorganosiloxane, fluorinated polydiorganosiloxane, or combination thereof that is hydroxyl-endblocked,
    (2) at least one polydiorganosiloxane, fluorinated polydiorganosiloxane, or combination thereof comprising at least three hydrosilyl moieties, and
    (3) at least one base selected from 1,8-diazabicyclo[5.4.0]-7-undecene (DBU), 1,5-diazabicyclo[4.3.0]-5-nonene (DBN), and combinations thereof;
  (b) providing at least one substrate having at least one major surface;
  (c) applying said curable polysiloxane composition to at least a portion of at least one said major surface of said substrate; and
  (d) allowing or inducing said curable polysiloxane composition to cure to form a release coating.

* * * * *

UNITED STATES PATENT AND TRADEMARK OFFICE
CERTIFICATE OF CORRECTION

PATENT NO. : 8,840,993 B2
APPLICATION NO. : 13/807326
DATED : September 23, 2014
INVENTOR(S) : Yu Yang It is certified that error appears in the above-identified patent and that said Letters Patent is hereby corrected as shown below:

In the specification

Column 1
Line 6, Delete "PCT/US2011/041180," and insert -- PCT/US2011/041181, --, therefor.

Column 9
Line 1, Delete "thereof" and insert -- thereof; --, therefor.

Column 9
Line 29 (Approx.), Delete "thereof" and insert -- thereof; --, therefor.

Column 12 (Structure)
Lines 26-32, Delete

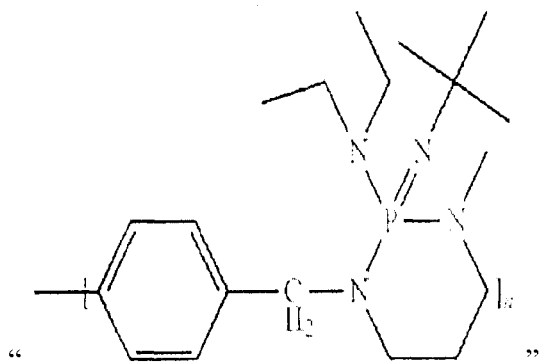

Signed and Sealed this
Twenty-first Day of April, 2015

Michelle K. Lee
*Director of the United States Patent and Trademark Office* and insert

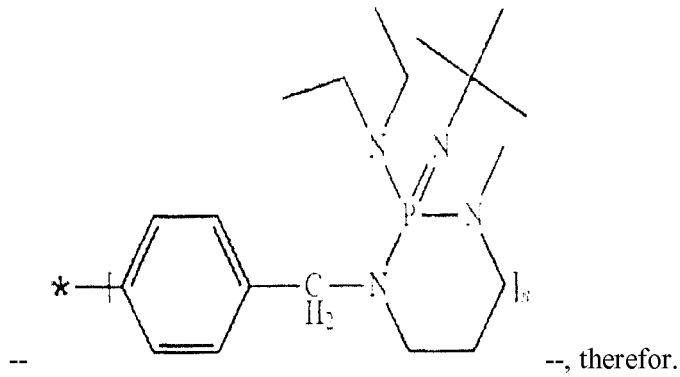

--                                                        --, therefor.

Column 16
Line 15 (Approx.), Delete "thereof" and insert -- thereof. --, therefor.

Column 24 (Example No. C-3) (Table 1- continued)
Line 1, Delete "N,N'-Diicyclohexylcarbodiimide" and insert
-- N,N'-Dicyclohexylcarbodiimide --, therefor.

Column 31
Line 36, Delete "supercalendared" and insert -- supercalendered --, therefor.

Column 31
Line 53, Delete "supercalendared" and insert -- supercalendered --, therefor.

Column 32
Line 4, Delete "supercalendared" and insert -- supercalendered --, therefor.